United States Patent [19]

Ament et al.

[11] 4,009,259

[45] Feb. 22, 1977

[54] IMMERSION METHOD FOR TREATING AQUATIC ANIMALS

[75] Inventors: Roland W. Ament, Arvada, Colo.; Daniel C. Fender, Seattle, Wash.

[73] Assignee: Wildlife Vaccines, Inc., Wheat Ridge, Colo.

[22] Filed: Oct. 3, 1975

[21] Appl. No.: 619,434

[52] U.S. Cl. .................................. 424/89; 424/88; 424/92; 424/128; 424/153

[51] Int. Cl.² ................ A61K 39/12; A61K 39/02; A61K 33/42

[58] Field of Search ............. 424/128, 153, 88, 89, 424/92

[56] References Cited

OTHER PUBLICATIONS

The Merck Veterinary Manual – 4th edition, (1973), pp. 1172–1173.

*Primary Examiner*—Sam Rosen
*Attorney, Agent, or Firm*—Beveridge, DeGrandi, Kline

[57] ABSTRACT

Hyperosmotic immersion method for treating water-living animals is disclosed. The animals are immersed in a hyperosmotic solution and thereafter are immersed in a health or welfare enhancing medium.

22 Claims, 6 Drawing Figures

EFFECT OF IMMERSION
TIME ON BSA INFUSION

EFFECT
OF VARYING BSA
CONCENTRATIONS
5.3 %NaCl
3 MIN. SOAK

EFFECT OF VARYING
NaCl CONCENTRATIONS 5.3% NaCl PRESOAK FOLLOWED 3 MIN. IN 2% BSA

EFFECTS OF PRE-SOAK

EFFECTS OF pH AND FISH SIZE ON INFUSION OF BSA

IMMERSION METHOD FOR TREATING AQUATIC ANIMALS

BACKGROUND OF THE INVENTION

Disease outbreaks have plaqued the fish industry through the years. With the growth of large scale fish culture facilities, economic losses due to disease have made their control imperative.

The world fisheries industry provides man with abundant, essential, protein-rich animal products. This harvest which is gathered by nearly all nations constitutes a basic food raw material for mankind. These commercial fisheries involve billions of dollars in the course of harvesting, processing, marketing and consumption of products. The value of the sports fishery, worldwide, is likewise substantial.

For a multitude of reasons, the commercial and sports fisheries are increasingly required to control disease problems to maintain fish populations. However, there are not presently available adequate techniques or tools for such disease control. Entire runs of fish in recent years have been substantially decimated, while others are now seriously threatened. Both hatchery and naturally propagated fish have experienced high losses, including losses to brood stocks.

Like other vertebrate animals, the young of fish are particularly susceptible to many highly infectious diseases. Obviously one cannot needle inject tiny fish on a commercial basis. A new and novel delivery system is a prerequisite to feasible drug and vaccine applications.

The problem is especially important when it is realized that serious salmon diseases may threaten the continued existence of the commercial salmon fishery as it has existed in the past. In fact, the overall future of salmon is of special concern. Today, highly prized sockeye salmon runs in California, Oregon and Washington streams appear to have been substantially damaged or destroyed. Heavy runs were recorded up to recent times. The sockeye has been the dominant economic fish species in Alaska. The Alaskan salmon pack, primarily sockeye, has in the past produced an estimated overall economic impact approaching $200 millions annually. However, recent sharp declines have been noted and fishing for this species was greatly restricted in 1974. Though the reason for these declines are varied and complex, disease is the factor which may have contributed to the recent declines.

Hatchery propagation of the sockeye species, though very desirable, has been seriously affected by one virus disease only recently identified and named. The disease is Infectious Hematopoetic Necrosis, abbreviated IHN. It is considered as one of the major causes for the damage to the sockeye runs in the Columbia river drainage system. During 1974, U.S. Fish and Wildlife Service testings indicated that IHN is widely distributed throughout Alaska in natural spawning sockeye salmon.

It is therefore highly desirable to provide an immunizing vaccine against the IHN disease. IHN is not a selective pathogen against the sockeye species. It now appears to be a serious threat to other anadromous salmonids and fresh-water trout. In the Sacramento River drainage system, salmon hatchery mortalities (in 1974) exceeded 90%; the cause is believed to be IHN. Here, the salmon species was the chinook. Of further concern is the reported indication that over 40% of the anadromous steelhead trout in this same river system carried an IHN infection.

Recently, this disease was detected in chinook returning to hatcheries in the Columbia River system. This is not really surprising since the IHN virus was prevalent in the heavy sockeye runs of the Columbia River before their substantial disappearance. If the Columbia River Chinook hatchery mortalities parallel the Sacramento River experience, this will be a problem of major regional consequences.

It is obvious, in view of the millions of dollars involved, that the West Coast states cannot afford to lose their salmon to any cause. With regard to disease, it appears now that only immunological procedures can provide the required long term, juvenile to adult, protection against viral and bacterial diseases of fish.

Various trout species have high sports and commercial value. These cold-water fish are much sought after. Infectious Pancreatic Necrosis (IPN) is one serious trout disease that significantly reduces trout populations. It is reported that the State of Oregon in both 1973 and 1974 lost much of the hatchery propagated trout stocks to this one disease.

Another viral disease is the highly infective and contagious Channel Catfish Virus Disease (CCVD). Here, the principal target market is catfish in commercial agriculture. During 1970, there were approximately 70,000 acres in catfish farm ponds in the U.S., mainly in the Southeast. Acreage planted to catfish has increased yearly the past decade. Fish are stocked at the rate of about 20,000/acre with market harvest in two years. Up to 500,000,000 fingerlings could require vaccination against CCVD annually in the U.S. There also appears to be a sizable sports propagated population of channel catfish available for vaccination.

Recognizing that there are numerous serious bacterial and fungal diseases presenting a health hazard to commercial and sports fish, it is believed that a serious need exists with respect to combating the diseases mentioned above as well as Furunculosis, caused by Aeromonas salmonicida, Vibriosis, caused by Vibrio anguillarum, and Enteric Redmouth Disease, caused by an Enterobacterium. Each disease is responsible for massive fish kills throughout the world. All salmonids would benefit from immunity to these serious bacterial diseases.

PRIOR METHODS

In the past few years, numerous attempts to vaccinate fish have had varying degrees of success. Bacterins and vaccines have been administered in the feed over prolonged periods of time with some degree of success. Bacterins, in other studies, have been added directly to the water in the fish holding tank with disappointing results. Attenuated or modified organisms have been added to water of the fish successfully; however, with the possibility of the organism reverting to virulence and "seeding" rivers, lakes, hatcheries, etc., this approach does not seem practical. Protection has been demonstrated in fish following parenteral injections of antigen. Because of economic reasons, "needle injection" is not normally warranted in fish production. However, many hatcheries have been forced to "hand inject" fish in an attempt to reduce the severe economic loss due to disease. Because of handling problems, this method has not been completely satisfactory.

SUMMARY OF THE INVENTION

Realizing the need for a method to economically deliver substances to fish with the least amount of stress, studies were conducted to develop a delivery system for the vaccination of fish. Bovine serum albumin (BSA) was selected as the antigen for use in evaluating various delivery systems since it is antigenic and has a molecular weight of 60,000

The general procedure for the hyperosmotic immersion process is to immerse the fish in a hyperosmotic solution and thereafter immerse the fish in the vaccine or other health and/or welfare enchancing agent. Chemotherapeutants may also be used.

Bovine serum albumin was first used in these studies to develop fundamental relationships of antigen "uptake" in the fish by vary techniques. The effectiveness of antigen delivery systems was determined by the recovery of bovine serum albumin from the serum of fish. The Rocket electrophoresis technique was used to quantify the BSA-serum concentrations. The Rocket electrophoresis technique consists of an agar plate containing BSA antiserum in the agar, unknown serum samples as well as a standard BSA in fish serum are placed in wells and allowed to migrate through the BSA-antiserum containing agar by electrophoresis. The quantity in the unknown sample is determined by reference to the migration of the known standard BSA-fish serum.

It has been determined that hyperosmotic solution greatly aids in the up-take of health and/or welfare enchancing agents into the serum of exposed fish. Numerous chemicals have been evaluated as hyperosmotic adjuvants for health and/or welfare enhancing agent influx into test fish. These are described in Table 1. All chemicals were screened in a similar manner; five trout fish were immersed in a 2% BSA solution with the test chemical for 3 minutes. Fish were tail bled 45 minutes later.

Due to the toxicity of the various chemicals, the concentrations used varied. Throughout these studies, the highest non-toxic concentration was used. Only NaCl and a 8% NaCl physiologically balanced buffered salt solution have been tested at concentrations in excess of 1650 mOsm (milliosmoles).

Results of chemical screening on the influx of a 2% BSA solution are presented in Table 1.

TABLE 1

RESULTS OF CHEMICAL SCREENING

| Chemical | 3 Min. Bath in 2% BSA + Chemical | | | | Std. Error |
|---|---|---|---|---|---|
| | pH* | % | mOsm | BSA/mg/ml | |
| Dextrose | 7.1 | 30 | 1650 | 14 | 1 |
| | 7.1 | 15 | 825 | 10 | 1 |
| Sucrose | 7.4 | 49 | 1650 | 38 | 4.5 |
| $CaCl_2$ | 7.4 | 8.25 | 1240 | 22 | 4 |
| $HCO_3$ | 7.7 | 4.9 | 800 | 53 | 10 |
| | 7.7 | 2.45 | 400 | 29 | 4 |
| KCl | 7.2 | 2 | 500 | 30 | 5 |
| | 7.2 | 0.8 | 200 | 15 | 5 |
| $MgCl_2$ | 7.5 | 2.8 | 400 | 44 | 8 |
| | 7.5 | 1.4 | 210 | 21 | 5 |
| PBS** | 7.2 | 1 | 275 | 20 | 3.4 |
| NaCl | 7.0 | 5.32 | 1650 | 145 | 19 |
| | 7.0 | 2.66 | 800 | 30 | 5 |
| Urea | 8.7 | 10 | 1650 | 26 | 8 |
| Methanol | 7.0 | 5 | — | 11 | 3 |
| PEG-6000 | 6.0 | 20 | — | 8 | 6 |
| DMSO+(dimethyl sulfoxide) | 7.2 | 10 | 3000 | 124 | 15 |
| 1650mOSM | 7.2 | 5 | 2300 | 107 | 9 |
| NaCl | 7.2 | 2.5 | 1900 | 189 | 15 |

*pH of chemical solution before addition of BSA.
**Phosphate buffered saline solution.

From the foregoing table, it has been concluded that the chemicals used in the hyperosmotic solutions function to prepare cell membranes of the aquatic animals for the transfer of substances with no biophysical change in the cell membrane For example, the macrophages are cells in the immunocompetent system of a living animal and will engulf foreign materials such as antigens. The hyperosmotic solutions facilitate the action of the macrophages in utilization of antigenic mass.

As a minimum threshold, a concentration of 1200 mOsm is effective and greater amounts may be used. The maximum amount is limited by the concentration that the water-living animal can withstand for 30 seconds to 3 minutes without substantial deleterious effect. Thus, the exposure time is related to the concentration of the hyperosmotic solution and toxic levels of concentration should be avoided.

Hyperosmotic effect with varying time and concentrations has also been determined.

Three studies were performed to determine the effect of immersion time, concentration of hyperosmotic (NaCl), and concentration of antigen (BSA) on the influx of BSA into the serum of the fish.

A standard test system consisting of 5.32% NaCl in phosphate buffered water with 2% BSA was used to gain these fundamental relationships. Fish were immersed in the standard solution for 3 minutes, then placed in holding containers supplied with water. Forty-five minutes after vaccination, the fish were tail bled.

The results of varying the immersion time that fish were exposed to the standard antigen solution are presented in FIG. 1. The limitation to length of bath time is mortality, which is possibly due to toxic effect of NaCl in the solution. Mortality first occurred at 4 minutes exposure, and 100% after 5 minutes. As a result, it has been concluded that the hyperosmotic pre-soak should range from 30 seconds to 2 minutes for optimum conditions. As long as 3 minutes can be tolerated, however.

The effect of varying BSA concentrations, in the standard test system, on the influx into the serum of the fish is presented in FIG. 2. It is apparent from this that antigen concentration in the vaccine-hyperosmotic system is important to the serum level obtained following immersion.

The results of varying NaCl concentrations in the standard test system are presented in FIG. 3. When the NaCl concentration of the hyperosmotic adjuvant varied, a sharp increase in serum BSA levels occurred between 2.8 and 5.6% NaCl. From 1.9 to 8.5% NaCl in water gives good results.

Additional tests indicate a very sharp increase in BSA-serum concentrations occurs at about 1400 mOsm NaCl. The 5.32% NaCl solution (1650 mOsm) is near the minimum threshold level. Other studies indicate an 8% NaCl buffered solution gives high level of BSA in the serum of the fish.

Also, it has been determined that about 3 minutes immersion time in the antigen or vaccine is optimum, with about 2 to about 5 minutes being a suitable range.

Due to the possibility of altering the antigenicity and consequently the immunogenicity of proteins in the presence of high salt solutions, a two-phase delivery system was evaluated. In the first phase, fish were exposed to the chemical accelerant, then removed and placed into the antigenic solution, in the second phase. FIG. 4 shows the results of this two-part delivery method. In this test, fish were immersed for varying times in the salt solution but all received a 3 minute bath in a 2% BSA solution. The implication is that this method represents a highly feasible delivery system. However, removing the protein from the salt accelerant causes some difficulty; apparently, the BSA reduces the toxicity of the NaCl; hence, the harshness of the salt alone is far greater than when in combination with BSA.

Recent studies indicate the pre-soak toxicity can be eliminated by 8% NaCl in phosphate buffered solution and deliver high levels of BSA in the serum of exposed fish.

All amounts indicated herein are by weight unless otherwise specified.

Results of immersion using 5.3% NaCl and 10% urea are shown in FIG. 5.

Using the standard test solution, the indicated pH of the solution was adjusted to 5, 7 and 9. Each of these solutions was administered in the standard manner. FIG. 6A shows the results. Because an increase in pH aids the movement of BSA into fish, bicarbonate ($HCO_3^-$) was added to the standard test solution at 4.3%. Although not quantified yet, the results indicate that the use of $HCO_3^-$ to elevate pH, and ionic strength increases the serum BSA concentration. Pre-soak tests using pH as a variable will aid in resolving what the pH effect is. Presently, pH is believed to either aid in the effect of NaCl; dehydration (weight loss equal to or greater than 2.87%) or possibly in an electrical charge attraction. Because BSA assumes a negative charge with increased pH, it may be plausible that fish are a net positive due to free $Na^{\pm}$ diffusion and hence the attraction of opposite charges. Best results are obtained when operating with a hypertonic solution with a PH range of about 7 to about 9.

The average weight of fish from which test fish are obtained is about 6 grams (75 fish/pound). This population ranges from slightly less than 1 gm to 8 gms. Therefore, due to great differences in individual fish BSA concentrations, size was considered as a possible factor. Fish were divided into three weight classes, 2 gm, 4 gm and 8 gm. The individual groups each received the standard test. FIG. 6B shows no correlation to susceptibility with weight in the range tested.

In order to evaluate the location of BSA, once infused into test fish, a pool of fish were given the standard test, then subsamples taken with increasing time from vaccination. Surprisingly, there is a very fast initial uptake resulting in about 20 $\mu$g/ml at zero time after vaccination. However, maximum concentrations of BSA are not reached until 45 to 60 minutes after the vaccination. Due to the slow release of BSA into the blood, it is reasonable to assume that the vaccinated fish harbor a pool of BSA which is either concentrated at some tissue other than blood or it is in some way disguised and in a non-antigenic form. The high serum-BSA levels are maintained and only slowly cleared over several days.

Due to the increase in serum-BSA with time, it is hypothesized that a reservoir exists at the point(s) of entry. Since it is known that fish drink in response to dehydration, it was assumed that the alimentary tract was the entry point. However, it has been unable to detect any BSA in the alimentary tract immediately after vaccinating with the standard test. Samples from the stomach indicate some vaccine material may be engulfed; however, it is apparently denatured. Forcing vaccine fluids into both the stomach and rectum by intubation gives zero serum-BSA levels.

The gills were looked at as a possible portal, and analyzed by sonicating the tissue in an equal weight of saline and analyzing the supernatant. One would expect initial high gill BSA levels and low serum levels, and this condition should reverse with time. Such was not the case; hence, the portal of entry may not be the fill. At this time, it was considered that the BSA may enter all at once into vaccinated fish, then end up in an internal organ. The anterior kidney, spleen and liver were all assayed for BSA; none of these organs contained sufficient concentrations to implicate them as reservoirs.

Recent studies indicate that the possible portal of entry of substances into fish utilizing the two-phase hyperosmotic adjuvant solution is between lateral lines. The lateral line of fish has small openings to the gills, laterally along both sides of the fish, as well as several openings in the head and gill region. The lateral lines are lined with cilia and contain large numbers of macrophages which possibly engulf antigens present in the lateral line system. The lateral lines lie adjacent to the lymphatic system which possibly is the route of entry of engulfed antigens into the blood system.

Fish treated by the standard system and immediately sacrificed showed no BSA in the blood, but extremely high levels (250 $\mu$g or greater) in the lateral lines. High levels of BSA were detected in the serum approximately 45 minutes after exposure to the antigen and at this time the concentration of BSA in the lateral lines had only slightly diminished.

It has been observed that the response of the test fish to the standard test conditions varies from day to day.

In the first stress experiment, 40 fish were held in a net out of water for 2 minutes. These were then pooled in a container with running water and subsamples taken over time and given the standard test greatment.

Another more direct stress was accomplished by injecting 10 $\mu$g of adrenlin, contained in 0.1 ml of PBS I.P. A control group was given 0.1 ml PBS alone I.P. These fish were given the standard test immediately after injection, or 10 minutes later to assure a full stress response. These results indicate that stress is a factor which inhibits immersion vaccine delivery and therefore its effect must be minimized. However, the tests also indicate differences for these two experiments given on different days. The reason for this daily change in population susceptibility to vaccination is not known. Also implied by these tests is that the gill, uner the control of the stress response is again not a portal of entry of the antigen. Reasoning that since the gill, much like mammalian lungs, increases in exchange area, increases blood flow and vascularity, it would be more likely to allow BSA entry under stress than when not under the stress response.

These tests indicate the portal of entry of the antigen following pre-soak in the hyperosmotic solution is by the lateral lines system of the fish. Large numbers of machophages found in the lateral lines possibly engulf the antigen which is forced into the lateral line system due to dehydration in the hyperosmotic solution, engulf the antigen and is absorbed into the adjacent lymphatic system and then into the blood of the fish.

The tests further establish that a two-phase delivery system, using a pre-soak in a hyperosmotic adjuvant solution (e. g., for approximately 2 minutes) followed by an immersion in the antigen solution (e. g., 3 minutes) appears to be a feasible system for delivery of substances into fish economically.

DETAILED DESCRIPTION OF OTHER ANTIGENS FOR USE IN THE INVENTION

Figure 1:
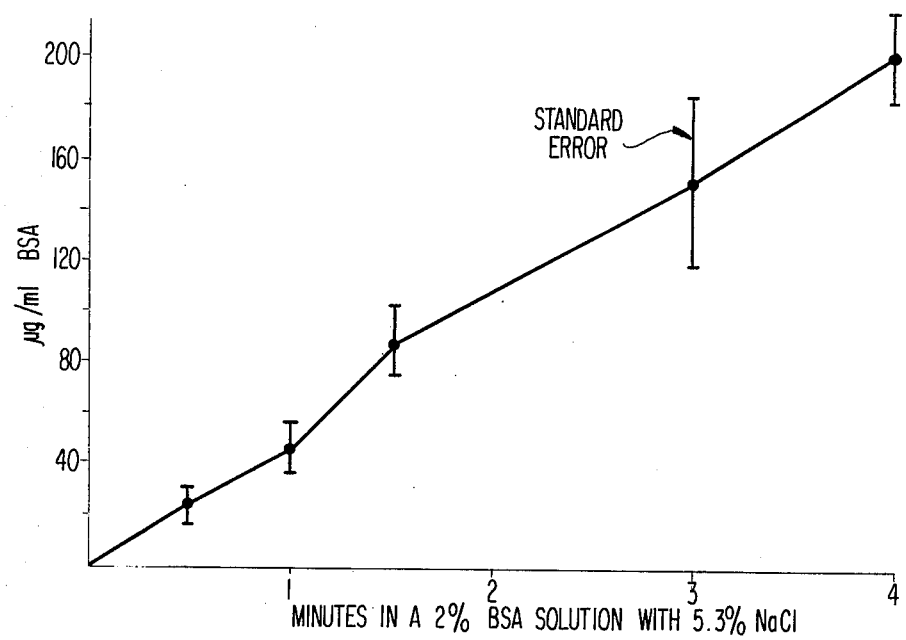
Figure 2:
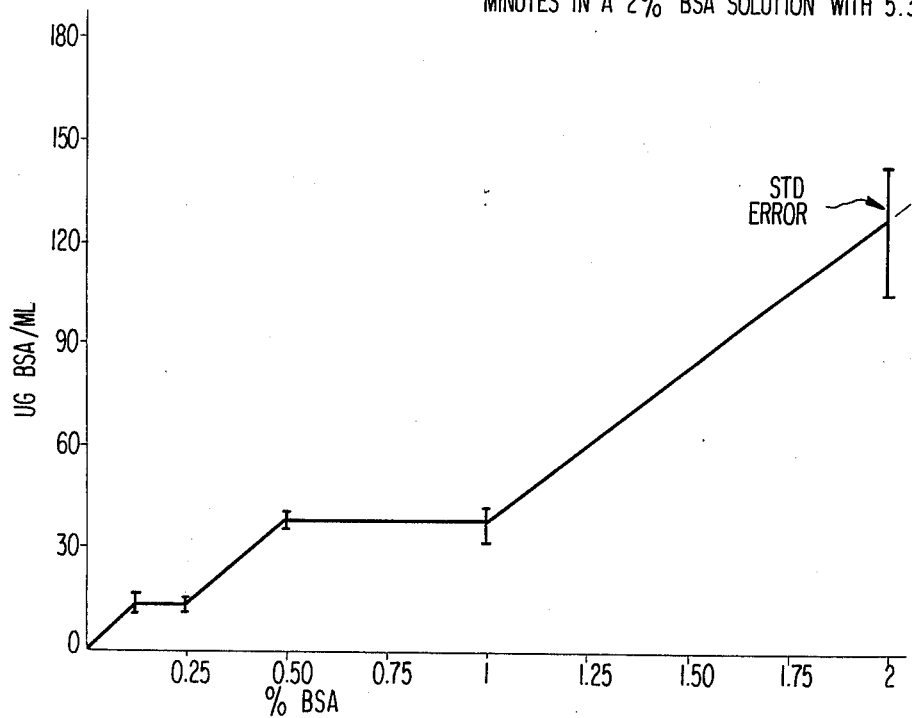
Figure 3:
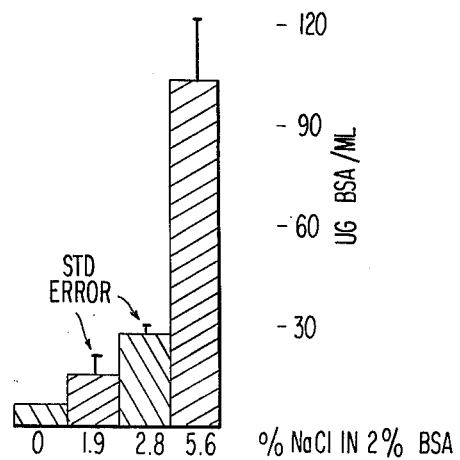
Figure 4:
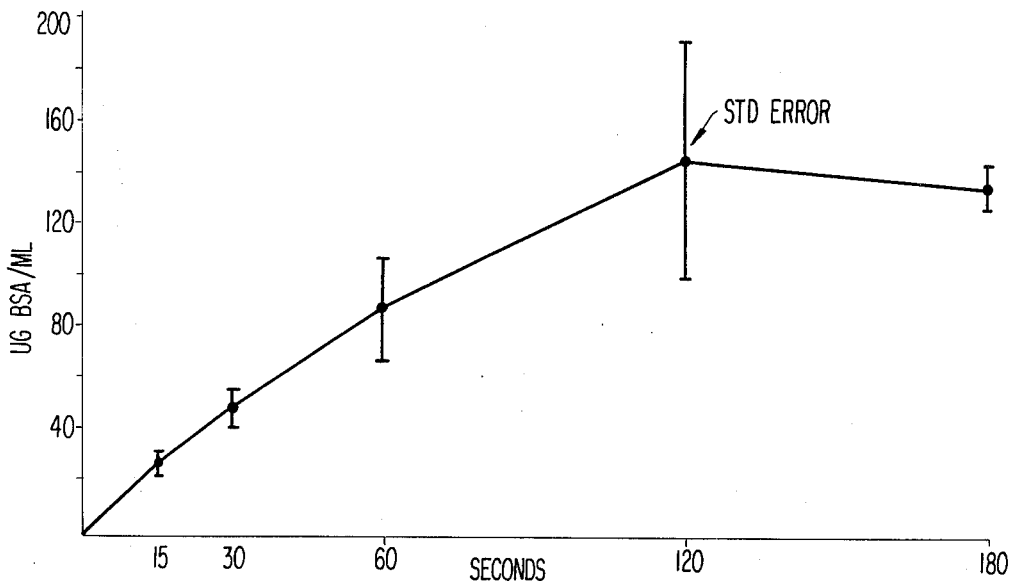
Figure 5:
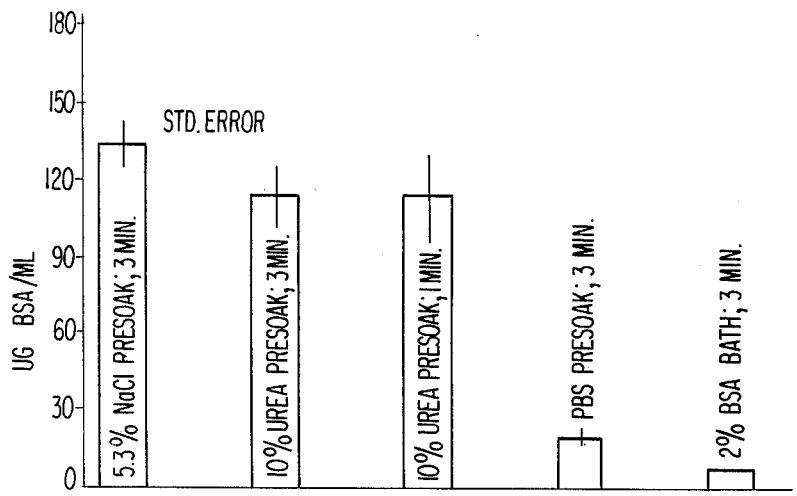
Figure 6:
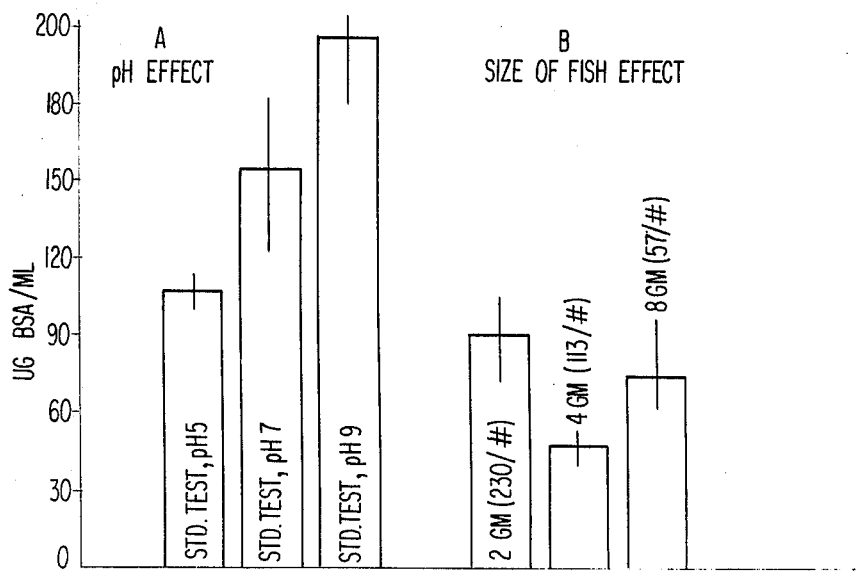

In order to illustrate the invention, a description of the production of a representative antigen suitable for purposes of immersion treatment will be set forth.

The product is produced from virulent Infectious Hematopoietic Necrosis (IHN) virus. The IHN virus was originally isolated from Rainbow Trout in Tacoma, Wash. The IHN virus was propagated in Fat Head Minnow (RHM) cell line cultures and has been passaged 3 times. The IHN Virus has remained virulent for the host animal. This strain of IHN virus is designated as Rainbow Trout Strain 1274. The complete vaccine contains 100% of Rainbow Trout Strain 1274 Infectious Hematopoietic Necrosis virus.

The IHN seed virus is identified by serum neutralization using special antiserum prepared in rabbits. The seed virus is also identified by its typical cytopathogenic effect in Fat Head Minnow (FHM) cell line cultures showing rounding of the cells and slight enlargement of the nucleus with Chromatin migration in the nucleus of the cell.

The Fat Head Minnow cell line is tested and must be satisfactory in accordance with 9 CFR 113.52. The master seed stock (86th passage) of the FHM cell and either each subculture of cells used to prepare the biological product or the final pool of harvested material is tested for sterility in accordance with 9 CFR 113.26 and for mycoplasma in accordance with 9 CFR 113.28.

The FHM cell line is grown in Eagle's MEM medium containing non-essential amino acids and sodium pyruvate containing 30 units of penicillin, 30 mcg of streptomycin sulfate and 2.5 mcg amphotericin B per ml with 10% sterile fetal calf serum.

The Fat Head Minnow cell line is subcultured by removing the monolayer culture by the addition of warm (30°–37° C) ATV solution. The resulting ATV cell suspension is centrifuged at 800 to 1500 RPM and the cells planted in sterile containers at a ratio of 3 to 1 in the growth medium described above. The cell cultures are incubated at 28° C ± 2° C for approximately 2 to 6 days or until monolayers are produced.

Maintenance medium for both seed and production virus propagation is Eagle's medium with non-essential pyruvates containing 30 units of penicillin, 30 mcg of streptomycin sulfate and 2.5 mcg amphotericin B per ml.

Infected tissue culture fluids are used for the inoculation of seed and production monolayer cultures. Seed culture fluids are prepared for inoculation by rapidly thawing in cool, running water both and is undiluted prior to use. To be considered satisfactory as seed, the virus must have a titer of at least 1,000 TCID$_{50}$ per ml.

The growth medium is aseptically removed from monolayer cultures of FHM cells to be inoculated. Both seed and production viruses are inoculated to the cell cultures and allowed to adsorb for 30 to 60 minutes. The following amount of virus is inoculated into each tissue culture flask monolayer; 0.5 ml to 5 ml for 32 oz. bottles, 10 ml to 25 ml into the 5 liter Vitex bottle, and 20 ml to 60 ml into the 9 liter roller drum bottle. Following the adsorption, approximately 100 ml. of maintenance medium described in II, C is added to the 32 ox culture bottle, 5 liter Vitex bottle, and 9 liter roller drum bottle, respectively.

The inoculated tissue culture bottles are incubated at 18° C ± 2° C for a period of 4 to 8 days following inoculation with the usual interval being 5 to 6 days.

Typical cytopathogenic effect due to the virus is observed usually in 5 to 7 days following incubation at 18° C ± 2° C. The cytopathogenic effect appears as rounding of the cells with a slight enlargement of the nucleus. Cultures are examined both microscopically and macroscopically for abnormal appearance of the cell or contamination.

On the day of harvest, the virus infected tissue culture bottles are removed from the incubator and observed carefully. Only bottles free of abnormal characteristics which might indicate contamination are harvested for production. The infected tissue cultures are harvested at 4 to 8 days following incubation.

The viral fluids are aseptically harvested from the tissue culture bottles into a sterile common container. Samples for testing are obtained from the virus pool. The harvested viral fluids are immediately inactivated with formaldehyde solution, at a final concentration of 0.05% (one volume of formaldehyde solution diluted 1 to 20 is added to 10 volumes of product). The inactivation period is at 28° C ± 2° C with intervals of agitation for at least 72 hours. At the end of the inactivation period, the cultures are moved into the in-process cooler.

The viral fluids are immediately inactivated with formaldehyde solution at a final concentration of 0.05% (1 volume of formaldehyde solution diluted 1 in 20 is added to 10 volumes of product). The period of inactivation is at 28° C ± 2° C for at least 72 hours with intervals of agitation.

Preservatives in the final product of vaccine are only the antibiotics used in the tissue culture fluids. The final product shall contain no more than 30 units of penicillin, 30 mcg of streptomycin sulfate and 2.5 mcg amphotericin B per ml.

Production pools of inactivated viral fluids found satisfactory for batching are aseptically pooled in a suitable sterile container which may be glass or stainless steel. The minimum acceptable virus pool titer prior to inactivation is $10^{5.5}$ TCID$_{50}$/0.2 ml and is blended with virus pools with high pre-inactivation titers so that final batch consists of at least $10^{6.0}$ TCID$_{50}$ per ml prior to inactivation.

Example of a Typical Serial

| Inactivated Virus Pools | Volume | Pre-Inactivation-Titers/ml |
|---|---|---|
| A | 25,000 ml | $10^{6.5}$ TCID$_{50}$ |
| B | 25,000 ml | $10^{6.5}$ TCID$_{50}$ |
| C | 50,000 ml | $10^{6.8}$ TCID$_{50}$ |
| Total | 100,000 ml | Average $10^{6.4}$ TCID$_{50}$ |

The preferred hyperosmotic solution has the following formulation.

| Ingredient | gms/liter |
|---|---|
| NaCl (analytical Reagent Grade) | 80.0 |
| KCl (analytical Reagent Grade) | 0.2 |
| Na$_2$HPO$_4$ (analytical Reagent Grade) | 1.15 |
| KH$_2$PO$_4$ (analytical Reagent Grade) | 0.2 |
| CaCl$_2$ (analytical Reagent Grade) | 0.1 |
| MgCl$_2$ · 6H$_2$O (analytical Reagent Grade) | 0.1 |
| Deionized H$_2$O | quantity sufficient to 1000 ml |

Preparation:
1. The NaCl, KCl, Na$_2$HPO$_4$ and KH$_2$PO$_4$ are dissolved in approximately 750 ml of deionized H$_2$O.
2. The CaCl$_2$ is dissolved in approximately 75 ml of deionized H$_2$O.
3. The MgCl$_2$ · 6H$_2$O is dissolved in approximately 75 ml of deionized H$_2$O.
4. The three solutions are mixed together in the order of preparation in a quantity sufficient to form 1 liter.
5. The solution is prepared in average quantities of 300 to 500 liters with a maximum of 650 liters.

The solution is sterilized by filtration through a .22 U millipore filter into a sterile common container.

Oxytetracycline HCl (as a commerical parenteral solution containing 10,000 mcg per ml) is added as a preservative to the batch at a final concentration of 30 mcg per ml in order to guard against accidental bacterial contamination of the hyperosmotic solution.

TREATMENT OF FISH

To test safety, thirty susceptible Rainbow Trout, 2½ to 3½ inches long, are placed in 1,000 ml of hyperosmotic adjuvant for 2 minute as a pre-soak in preparation for vaccination. The fish are then removed from the pre-soak and allowed to drip dry, then placed in 500 to 1,000 ml vaccine and allowed to swim for 2 to 3 minutes. After vaccination, the fish are placed in a holding aquarium and held for 14 days in 5°-15° C water.

At this time, the fish may be given a second vaccination. They are returned to the holding aquarium and held an additional 14 days for observation. To be a valid safety test, 27 fish must survive.

To test potency, twenty-five of the vaccinated fish from the test are placed in an aquarium in 5°-15° C water and held for 14 days. Twenty-five susceptible non-vaccinated fish are placed in a separate aquarium to serve as controls. At the end of the 14 day holding period, vaccinated and control fish are challenged intramuscularly with 0.05 ml of virulent challenge culture of IHN virus containing approximately 4 LD$_{50}$. To be satisfactory, 60% of the vaccinated fish must survive and 70% of the control fish must die within a 14 day observation period.

The vaccine prepared as outlined above is recommended for the prevention of Infectious Hematopoietic Necrosis infections in healthy salmonids from button-up stage and older.

The product is administered by placing fish, which have not been fed for 24 hours, in a tank containing the hyperosmotic adjuvant solution at a rate of one pound of fish per liter. The fish are allowed to pre-soak in the hyperosmotic solution for 30 seconds to 3 minutes then removed and allowed to "drip-dry." The fish are then placed in a tank containing the IHN vaccine, at the rate of one pound of fish per liter of vaccine, and allowed to swim for 2 to 3 minutes. The fish are removed from the vaccine, allowed to drip-dry and returned to their holding tank. A second vaccination procedure is recommended 14 to 21 days following the first vaccination. By the term drip-dry, we mean draining excess fluid.

The temperature of the hyperosmotic adjuvant solution and IHN vaccine should not vary ± 5° C from the temperature of the water in the holding tanks. The product is stored at 2° to 8° C.

This procedure can be repeated with comparable weights of fish using the same tank of hyperosmotic adjuvant solution and tank of IHN vaccine for 10 consecutive times. After the tenth usage, the product is discarded.

In another example, Enteric Redmouth bacteria may be used to treat fish. The bacteria used for the production of this product is the Hagerman strain of Enteric Redmouth (ERM). It is an unclassified entero-bacterium originally isolated from moribund Rainbow Trout in the Hagerman Valley region of Idaho in 1970. It has been passaged 30 times in tryptose soy broth and has retained its virulents for the host animal.

Each lot of working and production seeds are identified by slide agglutination test using specific antiserum prepared in rabbits. The virulence of the master seed is demonstrated by its ability to produce the disease in susceptible fish. The virulence of the organism is maintained by preparing a new master seed every 6 months by inoculating susceptible fish with current master seed bacteria. When the inoculated fish show typical disease, the bacteria is aseptically re-isolated from kidney tissue in sterile nutrient agar plates. Typical colonies are selected and inoculated into sterile nutrient broth.

Production cultures are produced in a continuous culture system with harvesting of cultures replenishing of medium occurring continuously or at intervals when turbidity determination made photometrically indicates the culture has at least $1 \times 10^9$ organisms per ml. The generation time of ERM bacterin in the logarithmic phase of growth is 7 to 11 minutes. The minimum length of the continuous culture lots is 12 hours with a maximum length of 120 hours.

Harvested bacterial cultures, in the common container, are lysed by the addition of 10N NaOH to a final pH of 8.7 to 9.3 until at least 80% of the intact bacteria are lysed as determined by centrifugation in a Hopkins tube at 1500 RPM. The pH of the culture is then adjusted to 7 to 7.4 by the addition of 10N HCl. During this adjusting period, most of the remaining intact bacteria will lyse. Formaldehyde solution is then added, during constant agitation, to a final concentration of 0.1%. The cultures are held at room temperature for a period of at least 48 hours and then transferred to the in-process cooler until batching.

Bacterin-Formaldehyde solution at a final concentration of 0.1% is added at the end of the lyse process. Oxytetracycline HCl, as a commercially prepared parenteral solution containing 10,000 mcg per ml, is added at the time of batching at a final concentration of 30 mcg per ml.

Safety and potency are tested as outlined above.

In a still further example, Vibrio anguillarum bacterin, 78-skid strain, was prepared. The bacteria used for the production of this product is Vibrio anguillarum. It was isolated from moribund chinnock salmon in Manchester Bay. It has been passaged seven times on tryptose soy agar and has remained virulent for the host animal. It was inoculated into susceptible fish and re-isolated and was passed once on tryptose soy agar.

The Vibrio anguillarum strain designated 78-SKID was obtained from the National Marine Fishery Service.

Typical Vibrio anguillarum colony growth on tryptose soy agar plates with regular colony margin is raised, confined, of white to yellow in color, non-fluorescent and has no diffusible pigment.

Production cultures are grown in a continuous culture system in pH controlled (by the addition of sterile 10N NaOH), mechanically and sterile air agitated, and turbidity monitored to determine the rate of harvest and addition of sterile medium to the vessel. No more than 600 liters of medium and harvested culture are prepared on continuous culture lot. The generation time of Vibrio anguillarum in logarithmic growth phase is approximately 12 to 20 minutes.

Throughout the continuous harvesting of the culture, turbidity is monitored to insure an 8% light transmission at 625 mu yield of culture. Samples are collected at the beginning and end of the continuous culture lots to test for purity and assayed for at least $1 \times 10^9$ organisms per ml by plate count to be considered satisfactory.

Production cultures are harvested from the continuous culture apparatus by sterile closed system into a common sterile glass vessel or stainless tank. Cultures are accumulated in this common vessel until the continuous culture lot is completed.

Harvested bacterial cultures, in the common container, are lysed by the addition of 10N NaOH to a final pH of 8.7 to 9.3 until at least 80% of the intact bacteria are lysed as determined by centrifugation in a Hopkins tube at 1500 RPM. The pH of the culture is then adjusted to 7 to 7.4 by the addition of 10N HCl. During this adjusting period, most of the remaining intact bacteria will lyse. Formaldehyde solution is then added, during constant agitation, to a final concentration of 0.1%. The cultures are held at room temperature for a period of at least 48 hours and then transferred to the in-process cooler until batching.

Bacterin — satisfactory harvested material from one or more lots are pooled together by aseptic technique into a common sterile stainless steel tank. The pH is adjusted to 7.0 to 7.4 by the addition of sterile 10N NaOH. Oxytetracycline HCl solution (10,000 mcg per ml) is added to the batch at a final concentration of 30 mcg per ml as a preservative for the solution.

Example of Typical Serial

| | |
|---|---|
| Inactivated *V. anguillarum* Culture Fluids | 600,000 ml |
| Oxytetracycline HCl solution | 1,800 ml |
| Formaldehyde solution | 600 ml |
| Total Serial | 602,400 ml |

Samples are collected at the time of batching for bulk potency and sterility, and the batch is refrigerated at 2° to 8° C until tests are complete and the product is filled into final containers.

Safety testing is carried out as follows:

Thirty susceptible Rainbow, 2½ to 3½ inches long, will be placed in 500 to 1,000 ml of hyperosmotic adjuvant for 30 seconds to 3 minutes as a pre-soak in preparation for vaccination. The fish are removed from the pre-soak and allowed to drip dry, then placed in 500 to 1,000 ml bacterin representative sample as formulated above and allowed to swim for 2 to 3 minutes. After vaccination, the fish are placed in a holding aquarium and held for 14 days in 5°–15° C water. At this time, the fish are given a second vaccination as described above. They are returned to the holding aquarium and held an additional 14 days for observation. To be a valid safety test, 27 fish must survive.

Potency is tested as follows:

Twenty-five of the vaccinated fish from the safety test are placed in an aquarium in 5°–15° C water and held for 14 days. Twenty-five susceptible non-vaccinated fish are placed in a separate aquarium to serve as controls. At the end of the 14-day holding period, vaccinated and control fish are challenged intramuscularly with 0.05 ml of virulent challenge culture of *V. anguillarum* bacteria containing approximately 4 $LD_{50}$. To be satisfactory, 60% of the vaccinated fish must survive and 70% of the control fish must die within a 14-day observation period.

The product Vibrio anguillarum bacterin, 78-skid strain, is administered by placing fish, which have not been fed for 24 hours, in a tank containing the hyperosmotic adjuvant solution at a rate of one pound of fish per liter. The fish are allowed to pre-soak in the hyperosmotic solution for 30 seconds to 3 minutes then removed and allowed to drip-dry. The fish are then placed in a tank containing the *V. anguillarum* bacterin, at the rate of one pound of fish per liter of bacterin, and allowed to swim for 2 to 3 minutes. The fish are removed from the bacterin, allowed to drip-dry and returned to their holding tank. A second vaccination procedure is recommended 14 to 21 days following the first vaccination.

This procedure can be repeated with comparable weights of fish using the same tank of hyperosmotic adjuvant solution and tank of *V. anguillarum* bacterin for 10 consecutive times. After the tenth usage, the product is discarded.

The temperature of the hyperosmotic adjuvant solution and Vibrio anguillarum bacterin should not vary ± 5° C from the temperature of the water in the holding tanks. The product is stored at 2° to 8° C.

Aeromonas salmonicida bacterin, C 74-11 strain, is another example of bacteria which may be used in accordance with this invention.

The bacteria used for the production of this product is *Aeromonas salmonicida*. It was isolated from moribund pink salmon at the Pacific Environmental Institute at West Vancouver, British Columbia. It has been passaged 6 times on tryptose soy agar, and has remained virulent for the host animal.

*Aeromonas salmonicida* stran designated C 74–11 was obtained from the Pacific Biological Station at Nanimo, British Columbia.

Typically, *Aeromonas salmonicida* colony growth on tryptose soy agar plates show some of the colonies which appear creamy and glistening with regular colony edges. After 72 hours of growth at 20° C ± 2° C, colonies produce a brown, water-soluble pigment that diffuses into the medium.

Production cultures are grown in a continuous culture system in PH controlled (by the addition of sterile 10N NaOH), mechanically and sterile air agitated, and turbidity monitored to determine the rate of harvest and addition of sterile medium to the vessel. No more than 600 liters of medium and harvested culture will be prepared on continuous culture lot.

The generation time of *Aeromonas salmonicida* is logarithmic growth phase is approximately 12 to 20 minutes.

Throughout the continuous harvesting of the culture, turbidity is monitored to insure a 16% light transmission at 625 mu yield of culture. Samples are collected at the beginning and end of the continuous culture lots to test for purity and assayed for at least $1 \times 10^9$ organisms per ml by plate count to be considered satisfactory.

Production cultures are produced in a continuous culture system with harvesting of cultures replenishing of medium occurring continuously or at intervals when turbidity determination made photomtrically indicates the culture has at least $1 \times 10^9$ organisms per ml. The minimum length of the continuous culture lots is 12 hours with a maximum length of 120 hours.

Production cultures are harvested from the continuous culture apparatus by sterile closed system into a common sterile glass vessel or stainless tank. Cultures are accumulated in this common vessel until the continuous culture lot is completed.

Harvested bacterial cultures, in the common container, are lysed by the addition of 10N NaOH to a final pH of 8.7 to 9.3 until at least 80% of the intact bacteria are lysed as determined by centrifugation in a Hopkins tube at 1500 RPM. The pH of the culture is then adjusted to 7 to 7.4 by the addition of 10N HCl. During this adjusting period, most of the remaining intact bacteria will lyse. Formaldehyde solution is then added, during constant agitation, to a final concentration of 0.1%. The cultures are held at room temperature for a period of at least 48 hours and then transferred to the in-process cooler until batching.

Bacterin — satisfactory harvested material from one or more lots are pooled together by aseptic technique into a common sterile stainless steel tank. The pH is adjusted to 7.0 to 7.4 by the addition of sterile 10N NaOH. Oxytetracycline HCl solution (10,000 mcg per ml) is added to the batch at a final concentration of 30 mcg per ml. as a preservative for the hyperosmotic solution.

Example of Typical Serial

| | |
|---|---|
| Inactivated *A. salmonicida* Culture Fluids | 600,000 ml |
| Oxytetracycline HCl solution | 1,800 ml |
| Formaldehyde Solution | 600 ml |
| Total Serial | 602,400 ml |

Samples are collected at the time of batching for bulk potency and sterility, and the batch is refrigerated at 2 to 8° C until tests are complete and the product is filled into final containers.

The final product (in 2 oz. bottles) is tested for and must be satisfactory for sterility in accordance with 9 CFR 113.26.

Safety and potency are tested as with other bacterins.

The product is administered by placing fish, which have not been fed for 24 hours, in a tank containing the hyperosmotic adjuvant solution at a rate of 1 pound of fish per liter. The fish are allowed to pre-soak in the hyperosmotic solution for 30 seconds to 3 minutes then removed and allowed to drip-dry. The fish are then placed in a tank containing the *A. salmonicida* bacterin, at the rate of 1 pound of fish per liter of bacterin, and allowed to swim for 2 to 3 minutes. The fish are removed from the bacterin, allowed to drip-dry and returned to their holding tank. A second vaccination procedure is recommended 14 to 21 days following the first vaccination.

This procedure can be repeated with comparable weights of fish using the same tank by hyperosmotic adjuvant solution and tank of *A. salmonicida* bacterin for 10 consecutive times. After the tenth usage, the product is discarded.

The temperature of the hyperosmotic adjuvant solution and *Aeromonas salmonicida* bacterin should not vary ± 5° C from the temperature of the water in the holding tanks. The product is stored at 2° to 8° C.

As the term health and/or welfare enhancing medium is used herein, it is intended to include antigens, vaccines, serums, bacterins, chemotherapeutants and the like which function to ultimately ring about an improvement in the health of the water-living animals. An antigen is a substance usually proteinaceous in nature which, when injected or taken in by a living organism, will bring about the formation of an immune response. Also, the term includes those substances which lessen incidence of disease or enable the creatures to ward off disease. Still further, the term welfare enhancing medium includes materials which may enable the animals to ward off predators or which contribute in some fashion to improving the welfare of the water-living animals. These health and/or welfare enhancing media or agents may also be considered as prophylactic and/or therapeutic agents against diseases of water-living animals, particularly, fish and shell fish. Anti-microbial agents, in general are useful against various bacteria, fungi and protozoa pathogenic to fish, shell fish and the like. Numerous viral and microbial infections of water-living animals can be treated in accordance with the method of this invention provided non-toxic amounts are used. Also, the agents must not be adversely effected by the hyperosmotic solutions used in the practice of this invention.

After treatment with the agent or media described herein, the animals may be returned to their natural habitat or to any other environment which simulates their natural environment, e. g., fish ponds, hatchery, etc.

The pH of the hyperosmotic solution should be no less than 5 and preferably 7 to 9 with a maximum of about 9.5.

Concentrations of the hyperosmotic solution in reference to 0.85% saline solution (physiological saline) can vary widely but should be a minimum concentration is limited only by animal tolerance levels.

The antigens should be in a concentration of $10^5$ to $10^{10}$ antigen particles per ml of vaccine solution.

It has been determined that chemotherapeutants can be administered utilizing the same procedures described for antigens without major modifications of the adjuvant or pre-soak methods. Molecular concentration of the chemotherapeutants may vary with their concentration or active ingredients and can be listed as follows:
1. antibiotics
2. antivirals
3. antimycotics
4. parasiticides
5. anhelmenthics The temperature of the hyperosmotic solution and the antigen material can vary, but in general, ambient conditions are selected. No special heating or cooling precautions need to taken.

Another hyperosmotic salt solution that is particularly useful in the practice of this invention has the following formulations:

| Ingredient | Amount |
|---|---|
| NaCl | 68 grams |
| KCl | 4 grams |
| $CaCl_2(2 . H_2O)$ | 2.65 grams |
| $MgSO_4(7 . H_2O)$ | 2 grams |
| $NaHPO_4(1 . H_2O)$ | 1.4 grams |
| Dextrose | 10 grams |
| $NaHCO_3$ | 22 grams |
| quantity sufficient to 1,000 ml with distilled $H_2O$ | |

While the detailed embodiment of this invention illustrates the two-step procees, it is within the purview of the inventors to conduct the process by cmbining the health and/or welfare enhancing agent together with the hyperosmotic solution and immersing the water-living creatures therein to obtain a beneficial result.

What is claimed is:
1. The method of treating water-living animals to impart a health and/or welfare enhancing agent thereto, which comprises contacting the water-living animals with a hyperosmotic solution and thereafter contacting the water-living animals with a health and/or welfare enhancing agent for a sufficient period of time for the water-living animals to absorb the said agent.
2. The method as set forth in claim 1 wherein the water-living animals are fish.
3. The method as set forth in claim 1 wherein the water-living animals are contacted with a hyperosmotic solution for 30 seconds to 3 minutes and then removed from the hyperosmotic solutions and contacted with an antigen for a period of time from 2 to 5 minutes and thereafter removing the water-living animals from the antigen.
4. The method as set forth in claim 1 wherein the water-living animals are contacted with a hyperosmotic solution for 30 seconds to 3 minutes and then removed from the hyperosmotic solution and contacted with a chemotherapeutant for a period of time from 2 to 5 minutes and thereafter removing the water-living animals from the chemotherapeutant.
5. The method of claim 3 wherein the antigen is Infectious hematopoietic necrosis.
6. The method of claim 3 wherein the antigen is Vibrio anguillarum bacterin.
7. The method of claim 3 wherein the antigen is Aeromonas salmonicida bacterin.
8. The method of claim 3 wherein the antigen is Bovine serum albumin vaccine.
9. The method of claim 3 wherein the antigen is Enteric Redmouth bacterin.
10. The method of claim 3 wherein the antigen is channel catfish virus vaccine.
11. The method of claim 3 wherein the antigen is Infectious pancreatic necrosis.
12. The method as set forth in claim 1 wherein the hyperosmotic solution is a solution comprising a minimum of 1200 mOsm of the solute.
13. The method as set forth in claim 12 wherein the solute is sodium chloride.
14. The method as set forth in claim 12 wherein the solute is urea.
15. The method set forth in claim 1 wherein the hyperosmotic solution is a solution having the following formulation:

| Ingredient | gms/liter |
|---|---|
| NaCl (analytical Reagent Grade) | 80. |
| KCl (analytical Reagent Grade) | 0.2 |
| $Na_2HPO_4$ (analytical Reagent Grade) | 1.15 |
| $KH_2PO_4$ (analytical Reagent Grade) | 0.2 |
| $CaCl_2$ (analytical Reagent Grade) | 0.1 |
| $MgCl_2 . 6H_2O$ (analytical Reagent Grade) | 0.1 |
| Deionized $H_2O$ | quantity sufficient to 1000 ml |

16. The method set forth in claim 1 wherein the hyperosmotic solution is a solution having the following formulation:

| Ingredient | gms/liter |
|---|---|
| NaCl | 68 grams |
| KCl | 4 grams |
| $CaCl_2(2.H_2O)$ | 2.65 grams |
| $MgSO_4(7.H_2O)$ | 2 grams |
| $NaHPO_4(1.H_2O)$ | 1.4 grams |
| Dextrose | 10 grams |
| $NaHCO_3$ | 22 grams |
| quantity sufficient to 1,000 ml with distilled $H_2O$ | |

17. A hyperosmotic solution used in the method of claim 1 which comprises a solution having the following formulation:

| Ingredient | gms/liter |
|---|---|
| NaCl (analytical Reagent Grade) | 80. |
| KCl (analytical Reagent Grade) | 0.2 |
| $Na_2HPO_4$ (analytical Reagent Grade) | 1.15 |
| $KH_2PO_4$ (analytical Reagent Grade) | 0.2 |
| $CaCl_2$ (analytical Reagent Grade) | 0.1 |
| $MgCl_2.6H_2O$ (analytical Reagent Grade) | 0.1 |
| Deionized $H_2O$ | quantity sufficient to 10000 ml |

18. A hyperosmotic solution used in the method of claim 1 which comprises a solution having the following formulation:

| Ingredient | gms/liter |
|---|---|
| NaCl | 68 grams |
| KCl | 4 grams |
| $CaCl_2(2 \cdot H_2O)$ | 2.65 grams |
| $MgSO_4(7 \cdot H_2O)$ | 2 grams |
| $NaHPO_4(1 \cdot H_2O)$ | 1.4 grams |
| Dextrose | 10 grams |
| $NaHCO_3$ | 22 grams |
| quantity sufficient to 1,000 ml with distilled $H_2O$ | |

19. A method of administering an antigen to fish which comprises contacting fish with a hyperosmotic solution at the rate of 10 lbs of fish per liter, thereafter permitting the fish to soak in the hyperosmotic solution for 30 seconds to 3 minutes and then removing the fish and contacting the fish with an antigen at the rate of 10 lbs of fish per liter of antigen and allowing the fish to swim in said antigen for 2 to 5 minutes, thereafter removing the fish from the antigen.

20. A method of administering a chemotherapeutant to fish which comprises contacting fish with a hyperosmotic solution at the rate of 10 lbs of fish per liter, thereafter permitting the fish to soak in the hyperosmotic solution for 30 seconds to 3 minutes and then removing the fish and contacting the fish with a chemotherapeutant at the rate of 10 lbs of fish per liter of chemotherapeutant and allowing the fish to swim in said chemotherapeutant for 2 to 5 minutes, thereafter removing the fish from the chemotherapeutant.

21. Method of treating water-living animals comprising immersing said animals in a hyperosmotic solution containing a health and/or welfare enhancing agent in a sufficient amount to be taken up by said animals.

22. A method of improving the health and/or welfare of water living animals comprising treating said animals with a hyperosmotic solution containing a health and/or welfare enhancing agent in a sufficient amount to be taken up by said animals.

* * * * *

Disclaimer and Dedication

4,009,259.—*Roland W. Ament*, Arvada, Colo. and *Daniel C. Fender*, Seattle, Wash. IMMERSION METHOD FOR TREATING AQUATIC ANIMALS. Patent dated Feb. 22, 1977. Disclaimer and dedication filed Feb. 10, 1981, by the assignee, *Wildlife Vaccines, Inc.*

Hereby disclaims and dedicates to the Public the entire remaining term of said patent.

[*Official Gazette March 24, 1981.*]